United States Patent [19]

Franz et al.

[11] 4,421,549

[45] Dec. 20, 1983

[54] AMIDO AND HYDRAZIDO DERIVATIVES OF N-TRIFLUOROACETYL-N-PHOSPHINO-THIOYLMETHYLGLYCINE ESTERS

[75] Inventors: John E. Franz, Crestwood; Robert J. Kaufman, University City, both of Mo.

[73] Assignee: Monsanto Company, St. Louis, Mo.

[21] Appl. No.: 107,209

[22] Filed: Dec. 26, 1979

[51] Int. Cl.$^3$ .................... A01N 57/12; A01N 57/14; A01N 57/16

[52] U.S. Cl. ........................................ 71/87; 560/16; 560/147; 544/157; 546/247; 548/412

[58] Field of Search ............... 71/87, 86; 560/16, 147, 560/19, 155; 544/157; 546/247; 548/412

[56] References Cited

U.S. PATENT DOCUMENTS

| | | |
|---|---|---|
| 3,799,758 | 3/1974 | Franz . |
| 4,047,926 | 9/1977 | Rueppel ................................ 71/86 |
| 4,067,719 | 1/1978 | Dutra ................................... 71/86 |
| 4,180,394 | 12/1979 | Franz et al. ............................ 71/86 |

OTHER PUBLICATIONS

Rueppel et al., Biomedical Mass Spectrometry, vol. 3 (1976), pp. 28–31.

*Primary Examiner*—Catherine L. Mills
*Attorney, Agent, or Firm*—Richard H. Shear; Arnold H. Cole

[57] ABSTRACT

This invention relates to a new class of organic chemical compounds. More particularly, this invention is concerned with amido and hydrazido derivatives of N-trifluoroacetyl-N-phosphinothioylmethylglycine.

This class of compounds has been found to be useful as intermediates in producing amido and hydrazido derivatives of N-phosphinothioylmethylglycine esters which show herbicidal activity. Some of the class of compounds of this invention also show herbicidal activity when applied to certain varieties of weeds or undesired plants.

21 Claims, No Drawings

AMIDO AND HYDRAZIDO DERIVATIVES OF N-TRIFLUOROACETYL-N-PHOSPHINOTHIOYL-METHYLGLYCINE ESTERS

This invention relates to a new class of organic chemical compounds. More particularly, this invention is concerned with amido and hydrazido derivatives of N-trifluoroacetyl-N-phosphinothioylmethylglycine wherein amido or hydrazido groups are bonded to the phosphorus atom in addition to a divalent sulfur atom. This class of compounds has been found to display desirable herbicidal activity when applied to certain varieties of weeds or undesired plants.

U.S. Pat. No. 3,799,758 describes the preparation of N-phosphonomethylglycine and certain of its esters, amides and salts. Also described is the use of such compounds as contact or post-emergent herbicides.

U.S. Pat. No. 3,991,095 describes derivatives of N-phosphonomethylglycine and salts thereof wherein there is a thiocarbonyl group attached to the nitrogen atom.

Biomedical Mass Spectrometry, Vol. 3, (1976) pages 28–31 describes the tributyl ester derivatives of N-trifluoroacetyl-N-phosphonomethylglycine.

It will be apparent from a study of the above patents and publication that none of them disclose or suggest amido or hydrazido N-trifluoroacetyl-N-phosphonomethylglycines containing a P=S grouping.

The compounds of the present invention are represented by the formula $$\underset{RO-\overset{O}{\overset{\|}{C}}-CH_2N-CH_2-\overset{S}{\overset{\|}{P}}\diagdown_{Z}^{Z}}{\overset{O=C-CF_3}{|}} \quad (I)$$

wherein R is a member of the class consisting of alkyl of from 1 to 8 carbon atoms, chloroalkyl of from 1 to 4 carbon atoms and from 1 to 3 chlorine atoms and alkoxyalkyl containing from 3 to 7 carbon atoms and wherein Z is a member of the class consisting of $$-\underset{|}{\overset{R'}{N}}-R'$$

wherein each R' is individually selected from the class consisting of hydrogen, $C_1$–$C_4$ alkyl, $C_2$–$C_4$ alkenyl, $C_3$–$C_7$ cycloalkyl, benzyl or phenyl; a heterocyclic group selected from the class consisting of morpholine, pyrrolidine or piperidine; or a $$\underset{N-Z_1}{\overset{H}{|}}$$

group wherein $Z_1$ is a $$N\diagup^{R''}_{\diagdown R''}$$

group wherein R'' is hydrogen, $C_1$–$C_4$ alkyl or phenyl; a heterocyclic group selected from the class consisting of piperidine, pyrrolidine and morpholine; or a $$\underset{N-\overset{O}{\overset{\|}{C}}-OCH_3}{\overset{H}{|}}$$

group. It is preferred that R be alkyl or chloroalkyl of from 1 to 4 carbon atoms. It is even more preferred that R be methyl or ethyl. It is preferred that Z represent alkylamino or dialkylamino of from 1 to 4 carbon atoms.

Illustrative of the alkyl groups represented by R are methyl, ethyl, n- and isopropyl, n-, sec, iso- and tert-butyl, pentyl, hexyl and octyl. The chloroalkyl groups that R represents are, for example, chloromethyl, chloroethyl, chloropropyl, trichloropropyl, chlorobutyl and the like.

Illustrative of the alkoxyalkyl groups which R represents are methoxyethyl, methoxypropyl, methoxybutyl, ethoxyethyl, ethoxypropyl, propoxyethyl, propoxypropyl and the like.

Illustrative of the alkyl groups represented by R' and R'' are methyl, ethyl, propyl, butyl, isobutyl and the like. Illustrative of the alkenyl groups represented by R' are vinyl, allyl, butenyl and the like. Illustrative of the cycloalkyl groups represented by R' are, for example, cyclopropyl, cyclobutyl, cyclopentyl, cyclohexyl and cycloheptyl.

In accordance with the present invention, the compounds of formula (I) are prepared by reacting a compound of the formula $$\underset{RO-\overset{O}{\overset{\|}{C}}-CH_2-N-CH_2-PCl_2}{\overset{O=C-CF_3}{|}} \quad (II)$$

wherein R is as above defined with an amine or hydrazine of the formula $$Z-H \quad \text{or} \quad \underset{N-Z_1}{\overset{H}{|}} \quad (III)$$

wherein Z and $Z_1$ are as above defined in the presence of a hydrogen halide acceptor and then treating the reaction mixture with at least an equivalent amount of elemental sulfur.

The above reaction is generally conducted at ambient temperature. However, temperatures in the range of from 0° C. to 50° C. can be employed. Ambient temperatures of from 15° C. to 25° C. are preferred for convenience.

If it is desired to produce compounds of formula (I) wherein each R' is different, it is necessary to perform sequential steps of esterification with the hydrogen halide acceptor. In each instance, one equivalent of the compound of the formula $$Z-H \quad \text{or} \quad H-\underset{|}{\overset{H}{N}}-Z_1$$

wherein Z and $Z_1$ are as above defined is added at each step.

It is, of course, apparent to those skilled in the art that for each chloro group in the compounds of formula (II), one should employ at least one equivalent of the amine or hydrazine of formula (III) together with at least an equivalent amount of the hydrogen halide acceptor.

Inasmuch as the dichlorophosphinyl compounds of formula (II) are unstable towards moisture, the reaction, for best results, must be conducted in an anhydrous environment, that is, anhydrous reagents and solvents should be employed. Although the reaction can be conducted in a stepwise manner, i.e., by isolating the dichloro compound of formula (II) and then conducting the amination and then subsequent conversion to the thioyl derivative, it is preferred for convenience to conduct the total reaction in a single reaction vessel without complete isolation and identification of the dichlorophosphinic compound.

The starting materials employed in the production of the compounds of the invention are prepared by the following general procedure.

An ester of N-hydroxyphosphinylmethylglycine is dissolved in trifluoroacetic acid and an equal molar quantity or slight excess of trifluoroacetic anhydride is added dropwise with stirring at ambient temperature. Too large an excess of anhydride should be avoided to obtain the best yields of the compound. The reaction mixture is then concentrated in vacuo to yield the ester of N-trifluoroacetyl-N-(hydroxyphosphinylmethyl)glycine.

The ester of N-trifluoroacetyl-N-(hydroxyphosphinylmethyl)glycine is then converted to the ester of N-trifluoroacetyl-N-[bis(chloro)phosphinomethyl]glycine by dissolving in benzene and then adding the mixture to excess phosphorus trichloride at ambient temperature. The phosphine dichloride is recovered by filtration and then concentration of the filtrate in vacuo.

The dichloro phosphine compound is extremely sensitive to moisture. It is, therefore, desirable and necessary to employ anhydrous reagents and aprotic solvents while protecting the reaction mixture from moisture to obtain the best yields.

The compounds of this invention are useful as herbicides or as intermediates in the preparation of herbicides, e.g., the trifluoroacetyl group can be removed by treating the compounds of the invention with sodium tetrahydridoboron in a solvent such as ethanol.

The following examples serve to further illustrate the invention. In the examples, all parts are parts by weight unless otherwise expressly set forth. All examples were run at ambient temperature (15° C.–25° C.) unless otherwise set forth.

EXAMPLE 1

N-trifluoroacetyl-N-(hydroxyphosphinylmethyl)glycine, 2-chloro ethyl ester, was converted to N-trifluoroacetyl-N-[bis(chloro)phosphinomethyl]glycine, 2-chloro ethyl ester, by dissolving in benzene and dropwise addition to a stirred solution of excess phosphorous trichloride. After stirring for five to ten minutes, the turbid solution was filtered and concentrated in vacuo to yield the phosphine dichloride (10.52 g, 0.0301 mol) which was taken up in tetrahydrofuran and to it was added dropwise with stirring a solution of dimethylamine (2.72 g, 0.0603 mol) and triethylamine (6.09 g, 0.0603 mol) in tetrahydrofuran (100 ml). The reaction was then stirred for two hours and 966 mg (0.0301 mol) of sulfur was added and then the stirring was continued overnight. The reaction was then filtered and concentrated to dryness. The residue was then dissolved in methanol and centrifuged to remove any unreacted sulfur; the supernatant liquid was decanted and concentrated to dryness. This residue was chromatographed on silica gel with ether to yield N-trifluoroacetyl-N-[bis(dimethylamino)phosphinothioylmethyl]glycine, 2-chloro ethyl ester (6.65 g) as a yellow oil, $N_D^{25} = 1.4750$, having the following analysis:

Calculated: C, 33.21; H, 5.07; N, 10.56. Found: C, 33.14; H, 5.10; N, 10.17.

EXAMPLE 2

N-trifluoroacetyl-N-(hydroxyphosphinylmethyl)glycine, 2-chloro ethyl ester, was converted to N-trifluoroacetyl-N-[bis(chloro)phosphinomethyl]glycine, 2-chloro ethyl ester, by dissolving in benzene and dropwise addition to a stirred solution of excess phosphorous trichloride. After stirring for five to ten minutes, the turbid solution was filtered and concentrated in vacuo to yield the phosphine dichloride (8.95 g, 0.0256 mole) which was taken up in tetrahydrofuran and to it was added dropwise with stirring a solution of 3.03 g (0.0513 mol) of isopropylamine and 5.18 g (0.0513 mol) of triethylamine in 100 ml of tetrahydrofuran. The reaction was then stirred for two hours and 822 mg (0.0256 mol) of sulfur was added and then the stirring was continued overnight. The reaction was then filtered and concentrated to dryness. The residue was then dissolved in methanol and centrifuged to remove any unreacted sulfur; the supernatant liquid was decanted and concentrated to dryness. The residue was chromatographed on silica gel with ether to yield N-trifluoroacetyl-N-[bis(isopropylamino)phosphinothioylmethyl]glycine, 2-chloro ethyl ester hemihydrate (6.1 g) as a brown oil, $N_D^{25} = 1.4805$, having the following analysis:

Calculated: C, 35.87; H, 5.74; N, 9.65. Found: C, 36.08; H, 5.57; N, 9.26.

EXAMPLE 3

N-trifluoroacetyl-N-(hydroxyphosphinylmethyl)glycine, 2-ethoxy ethyl ester, was converted to N-trifluoroacetyl-N-[bis(chloro)phosphinomethyl]glycine, 2-ethoxy ethyl ester, by dissolving in benzene and dropwise addition to a stirred solution of excess phosphorous trichloride. After stirring for five to ten minutes, the turbid solution was filtered and concentrated in vacuo to yield the phosphine dichloride (5.88 g, 0.0164 mol) which was taken up in tetrahydrofuran and to it was added dropwise with stirring a solution of 2.34 g of pyrrolidine and 3.3 g of triethylamine (0.0328 mol) in 50 ml of tetrahydrofuran. The reaction was then stirred for two hours and 525 mg (0.0164 mol) of sulfur was added and then the stirring was continued overnight. The reaction mixture was then filtered, concentrated to dryness, dissolved in methanol, centrifuged and concentrated in vacuo. The residue was then extracted with ether and the ether layer was decanted and concentrated to dryness. N-trifluoroacetyl-N-[bis-(pyrrolidino)phosphinothioylmethyl]glycine hemihydrate (1.5 g) was recovered as a brown oil, $N_D^{25} = 1.5004$, having the following analysis:

Calculated: C, 43.54; H, 6.40; N, 8.96. Found: C, 43.57; H, 6.27; N, 9.39.

EXAMPLE 4

N-trifluoroacetyl-N-(hydroxyphosphinylmethyl)glycine, octyl ester, was converted to N-trifluoroacetyl-n-[bis(chloro)phosphinomethyl]glycine, octyl ester, by dissolving in benzene and dropwise addition to a stirred solution of excess phosphorous trichloride. After stirring for five to ten minutes, the turbid solution was filtered and concentrated in vacuo to yield the phosphine dichloride (8.8 g, 0.022 mol) which was taken up in tetrahydrofuran and to it was added dropwise with stirring a solution of 5.35 g of N-methyl-N-benzylamine (0.044 mol) and 4.46 g of triethylamine (0.044 mol) in 40 ml of tetrahydrofuran. The reaction was then stirred for two hours and 707 mg (0.022 mol) of sulfur was added, and then the stirring was continued overnight. The reaction was then filtered and concentrated to dryness. The residue was then dissolved in methanol and centrifuged to remove any unreacted sulfur; the supernatant liquid was decanted and concentrated to dryness to yield 11.25 g of oil, of which 500 mg was chromatographed on silica gel with dichloromethane to yield analytical N-trifluoroacetyl-N-[bis(N-methyl-N-benzylamino)phosphinothioylmethyl]-glycine, octyl ester, as an oil, $N_D{}^{25} = 1.5584$, having the following analysis:

Calculated: C, 58.08; H, 6.89; N, 7.01. Found: C, 58.15; H, 6.91; N, 7.00.

EXAMPLE 5

N-trifluoroacetyl-N-(hydroxyphosphinylmethyl)-glycine, 2-chloroethyl ester, was converted to N-trifluoroacetyl-N-[bis(chloro)phosphinomethyl]glycine, 2-chloroethyl ester, by dissolving in benzene and dropwise addition to a stirred solution of excess phosphorous trichloride. After stirring for five to ten minutes, the turbid solution was filtered and concentrated in vacuo to yield the phosphine dichloride (10.1 g, 0.0289 mol) which was taken up in tetrahydrofuran and to it was added dropwise with stirring a solution of 5.05 g (0.058 mol) of morpholine and 5.85 g of triethylamine (0.0579 mol) in 100 ml of tetrahydrofuran. The reaction was then stirred for two hours and 927 mg (0.0289 mol) of sulfur was added and then the stirring was continued overnight. The reaction was then filtered, concentrated to dryness and dissolved in methanol. No sulfur was visible so it was not centrifuged. Instead, crystals were allowed to form as the methanol evaporated. A 1 g portion of the crystals was chromatographed on silica gel with ether to yield N-trifluoroacetyl-N-[bis(morpholino)phosphinothioylmethyl]glycine, methyl ester, (680 mg) as a white solid, m.p. 121°-122° C., having the following analysis:

Calculated: C, 38.78; H, 5.31; N, 9.69. Found: C, 38.48; H, 5.22; N, 9.40.

Evidently, the 2-chloroethyl ester was converted to the methyl ester during the reaction.

EXAMPLE 6

N-trifluoroacetyl-N-(hydroxyphosphinylmethyl)-glycine, butyl ester, was converted to N-trifluoroacetyl-N-[bis(chloro)phosphinomethyl]glycine, butyl ester, by dissolving in benzene and dropwise addition to a stirred solution of excess phosphorous trichloride. After stirring for five to ten minutes, the turbid solution was filtered and concentrated in vacuo to yield the phosphine dichloride (9.78 g, 0.0285 mol) which was taken up in tetrahydrofuran and to it was added dropwise with stirring a solution of 5.55 g of diallylamine and 5.77 g of triethylamine (0.057 mol). The reaction was then stirred for two hours and 915 mg (0.0285 mol) of sulfur was added and then the stirring was continued overnight. The reaction was then filtered, and concentrated to dryness. The residue was then dissolved in methanol and centrifuged to remove any unreacted sulfur; the supernatant liquid was decanted and concentrated to dryness. A portion of the residue (4 g) was chromatographed on silica gel with dichloromethane to yield N-trifluoroacetyl-N-[bis(diallylamino)phosphinothioylmethyl]glycine, butyl ester, (2.5 g) as a yellow oil, $N_D{}^{25} = 1.4882$, having the following analysis:

Calculated: C, 50.90; H, 6.71; N, 8.48. Found: C, 51.04; H, 6.72; N, 8.49.

EXAMPLE 7

N-trifluoroacetyl-N-(hydroxyphosphinylmethyl)-glycine, ethyl ester (2 g, 0.0072 mol), was dissolved in benzene and added to phosphorous trichloride dropwise with stirring. The liquid was filtered and the supernatant liquid evaporated under vacuum to yield N-trifluoroacetyl-N-carboethoxymethylaminomethylphosphine dichloride. The dichloride was dissolved in tetrahydrofuran and a solution of 2.91 g (0.0288 mol) of di-n-propylamine in tetrahydrofuran was added dropwise with stirring. After stirring for two hours, 134 mg (0.0072 mol) of sulfur was added and the reaction stirred overnight. The reaction was then filtered and concentrated to dryness. The residue was dissolved in methanol and centrifuged to remove the unreacted sulfur; the supernatent liquid was decanted and concentrated to dryness. The residue was dissolved in ether and washed with 5% aqueous sodium bicarbonate and hydrochloric acid, then dried over magnesium sulfate, filtered and concentrated to dryness. The residue was chromatographed on silica gel with hexane, then dichloromethane, then ether to yield N-trifluoroacetyl-N-[bis(di-n-propylamino)phosphinothioylmethyl]-glycine, ethyl ester, as a brown oil, $N_D{}^{25} = 1.5724$, having the following analysis:

Calculated: C, 47.99; H, 7.84; N, 8.84. Found: C, 47.46; H, 7.93; N, 8.74.

EXAMPLE 8

N-trifluoroacetyl-N-(hydroxyphosphinylmethyl)-glycine, ethyl ester (2.0 g, 0.0072 mol), was converted to its phosphine dichloride as in Example 7. The dichloride was dissolved in tetrahydrofuran and a solution of 1.71 g of n-propylamine (0.0288 mol) in tetrahydrofuran was added dropwise with stirring. After stirring for two hours, 134 mg (0.0072 mol) of sulfur was added and the reaction stirred overnight. The reaction was then filtered and concentrated to dryness. The residue was dissolved in methanol and centrifuged to remove the unreacted sulfur; the supernatant liquid was decanted and concentrated to dryness. The residue was dissolved in ether and washed with 5% aqueous sodium bicarbonate and hydrochloric acid, then dried over magnesium sulfate, filtered, and concentrated to dryness. The residue was extracted many times with petroleum ether, filtered and concentrated to dryness to yield N-trifluoroacetyl-N-[bis(n-propylamino)phosphinothioylmethyl]glycine, ethyl ester (1.15 g), as a yellow oil, $N_D{}^{25} = 1.4783$, and having the following analysis:

Calculated: C, 39.89; H, 6.44; N, 10.73; S, 8.19. Found: C, 39.57; H, 6.67; N, 10.97; S, 8.06.

EXAMPLE 9

N-trifluoroacetyl-N-[bis(chloro)phosphinomethyl]glycine, ethyl ester, was prepared as in Example 7. The phosphine dichloride thus obtained (0.71 g, 0.0023 mol) was dissolved in 10 ml of tetrahydrofuran and to it a solution of 0.84 g (0.0092 mol) aniline in 10 ml of tetrahydrofuran was added dropwise with stirring. After stirring for two hours, 72 mg (0.0023 mol) of sulfur was added and the reaction stirred overnight. The reaction was centrifuged and the supernatant liquid was decanated and concentrated in vacuo. The resulting oily residue was extracted with boiling petroleum ether and concentrated to yield N-trifluoroacetyl-N-[bis(anilino)-phosphinothioylmethyl]glycine, ethyl ester, as a brown oil, $N_D^{25} = 1.4992$, and having the following analysis:

Calculated: C, 49.67; H, 4.61; N, 9.15. Found: C, 49.83; H, 4.72; N, 9.03.

EXAMPLE 10

N-trifluoroacetyl-N-[bis(chloro)phosphinomethyl]glycine, ethyl ester, was prepared as in Example 7. The phosphine dichloride thus obtained from 2 g of N-trifluoroacetyl-N-(hydroxyphosphinylmethyl)glycine, ethyl ester (0.0072 mol), was dissolved in tetrahydrofuran and to it a solution of 2.11 g of n-butylamine in tetrahydrofuran was added dropwise with stirring. After stirring for one hour, 134 mg (0.0042 mol) of sulfur was added and the solution stirred overnight. The hydrochloride salts were filtered off and the supernatant liquid concentrated to dryness. This residue was extracted into petroleum ether, filtered, and concentrated in vacuo to yield 1.7 g of a crude product. This crude product was dissolved in methanol and centrifuged to remove unreacted sulfur. The supernatant liquid was concentrated in vacuo to yield N-trifluoroacetyl-N-[bis(butylamino)phosphinothioyl-methyl]glycine, ethyl ester (1.4 g), as a brown oil, $N_D^{25} = 1.5036$, and having the following analysis:

Calculated: N, 10.02; S, 7.64. Found: N, 9.71; S, 7.30.

N-trifluoroacetyl-N-[bis(chloro)phosphinomethyl]glycine, ethyl ester, was prepared from 3 g (0.0108 mol) of the N-(hydroxyphosphinyl) compound as in Example 7. The phosphine dichloride thus obtained was dissolved in tetrahydrofuran and to it a solution of 2.98 g (0.0432 mol) of diallylamine in 25 ml of tetrahydrofuran was added dropwise with stirring. After one hour, 340 mg of sulfur (0.0108 mol) was added and the reaction stirred overnight. The amine salts were then filtered off and the supernatant concentrated in vacuo. The residue was dissolved in methanol, centrifuged and the methanol solution evaporated to dryness. The oily residue thus obtained was extracted with hot petroleum ether and concentrated to dryness to yield N-trifluoroacetyl-N-[bis(diallylamino)-phosphinothioylmethyl]glycine, ethyl ester, as a yellow oil, $N_D^{25} = 1.5565$, and having the following analysis:

Calculated: C, 48.81; H, 6.25; N, 8.99; S, 6.86. Found: C, 48.71; H, 6.20; N, 9.06; S, 7.33.

EXAMPLE 12

N-trifluoroacetyl-N-(hydroxyphosphinylmethyl)-glycine, ethyl ester (4 g, 0.0145 mol), was converted into its phosphine dichloride as in Example 7. The dichloride was dissolved in tetrahydrofuran and a solution of 4.125 g of pyrrolidine (0.0580 mol) in tetrahydrofuran was added dropwise with stirring. After one hour, 463 mg (0.0145 mol) of sulfur was added and the reaction stirred overnight. The amine salts were filtered off and the solution concentrated to dryness in vacuo. The oily residue was then taken up in ether and washed with 10% aqueous potassium bicarbonate, 10% aqueous hydrochloric acid and then dried over magnesium sulfate, filtered and concentrated in vacuo to yield N-trifluoroacetyl-N-[bis(pyrrolidino)phosphinothioylmethyl]glycine, ethyl ester, as a brown oil, $N_D^{25} = 1.500$, and having the following analysis:

Calculated: C, 43.37; H, 6.07; N, 10.12; S, 7.72; P, 7.46. Found: C, 43.13; H, 5.98; N, 10.08; S, 7.84; P, 7.50.

EXAMPLE 13

N-trifluoroacetyl-N-(hydroxyphosphinylmethyl)-glycine, ethyl ester (10.2 g, 0.0368 mol), was converted into its phosphine dichloride as in Example 7. The dichloride was dissolved in tetrahydrofuran and a solution of 3.31 g (0.0736 mol) of ethylamine and 7.4 g (0.0736 mol) of triethylamine in tetrahydrofuran was added dropwise with stirring and the solution stirred for one hour, after which 1.17 g of sulfur (0.0368 mol) was added and the solution stirred overnight. The reaction mixture was then filtered and concentrated to dryness. The oily residue was dissolved in methanol and the unreacted sulfur was centrifuged out; the supernatant liquid was decanted and concentrated to dryness. The residue was taken up in ether and washed with 5% aqueous hydrochloric acid, 5% aqueous sodium bicarbonate, dried over magnesium sulfate and extracted with cyclohexane and then concentrated to yield N-trifluoroacetyl-N-[bis(ethylamino)phosphinothioylmethyl]glycine, ethyl ester, as an oil, $N_D^{25} = 1.5587$, and having the following analysis:

Calculated: C, 36.36; H, 5.83; N, 11.57; P, 8.52; S, 8.82. Found: C, 36.46; H, 5.84; N, 11.37; P, 8.43; S, 8.97.

EXAMPLE 14

N-trifluoroacetyl-N-(hydroxyphosphinylmethyl)-glycine, ethyl ester (10 g; 0.0360 mol), was converted into its phosphine dichloride as in Example 7. The dichloride (0.0137 mol) was dissolved in tetrahydrofuran and a solution of 1.62 g of isopropylamine (0.0275 mol) and 2.77 g (0.0275 mol) of triethylamine in tetrahydrofuran was added dropwise with stirring. After stirring for two hours, 439 mg of sulfur (0.0137 mol) was added and the reaction stirred overnight. The reaction was then filtered, concentrated to dryness, dissolved in methanol and centrifuged (to remove unreacted sulfur) and the supernatant liquid decanted and concentrated to dryness. The residue was dissolved in ether and washed with 5% aqueous sodium bicarbonate and hydrochloric acid, dried over magnesium sulfate, filtered and concentrated to dryness. The residue was extracted with cyclohexane and concentrated to dryness to yield N-trifluoroacetyl-N-[bis(isopropylamino)phosphinothioylmethyl]glycine, ethyl ester, as a brown solid, m.p. 54°-69° C., and having the following analysis:

Calculated: C, 39.89; H, 6.44; N, 10.74; P, 7.91; S, 8.19. Found: C, 39.71; H, 6.35; N, 10.72; P, 7.83; S, 8.05.

EXAMPLE 15

N-trifluoroacetyl-N-(hydroxyphosphinylmethyl)-glycine, ethyl ester (10 g; 0.0360 mol), was converted into its phosphine dichloride as in Example 7. The dichloride (0.0118 mol) was dissolved in tetrahydrofuran and a solution of 2.35 g of cyclohexylamine (0.0236 mol) and 2.40 g of triethylamine (0.0236 mol) in tetrahydrofuran was added dropwise with stirring. After stirring for two hours, 379 mg (0.0119 mol) of sulfur was added and the reaction stirred overnight. The reaction was then filtered and concentrated to dryness. The residue was dissolved in methanol and centrifuged to remove the unreacted sulfur; the supernatant liquid was decanted and concentrated to dryness. The residue was dissolved in ether and washed with 5% aqueous sodium bicarbonate and hydrochloric acid, then dried over magnesium sulfate, filtered and concentrated to dryness. The residue was chromatographed on silica gel to yield N-trifluoroacetyl-N-[bis(cyclohexylamino)phosphinothioylmethyl]]glycine, ethyl ester hemihydrate, as a tan solid, m.p. 52°-62° C., and having the following analysis:

Calculated: C, 47.50; H, 7.08; N, 8.75. Found: C, 47.30; H, 6.82; N, 8.35.

EXAMPLE 16

N-trifluoroacetyl-N-(hydroxyphosphinylmethyl)-glycine, ethyl ester, was converted into its phosphine dichloride as in Example 7. The dichloride (0.0250 mol) was dissolved in tetrahydrofuran and a solution of 5.43 g of phenylhydrazine (0.0505 mol) and 5.1 g of triethylamine (0.0505 mol) in tetrahydrofuran was added dropwise with stirring. After stirring for two hours, 800 mg (0.0250 mol) of sulfur was added and the reaction stirred overnight. The reaction was then filtered and concentrated to dryness. The residue was dissolved in methanol and centrifuged to remove the unreacted sulfur; the supernatant liquid was decanted and concentrated to dryness. The residue was dissolved in ether and washed with 5% aqueous sodium bicarbonate and hydrochloric acid, then dried over magnesium sulfate, filtered and concentrated to dryness. The residue was extracted with cyclohexane and concentrated to dryness, then chromatographed on silica gel with ether to yield N-trifluoroacetyl-N-[bis(N-phenylhydrazino)phosphinothioylmethyl]glycine, ethyl ester (2.4 g) as a solid, m.p. 115°-126° C., and having the following analysis:

Calculated: C, 46.62; H, 4.74; N, 14.31; P, 6.33; S, 6.55. Found: C, 46.56; H, 4.67; N, 14.15; P, 6.11; S, 6.40.

EXAMPLE 17

N-trifluoroacetyl-N-(hydroxyphosphinylmethyl)-glycine, ethyl ester (12.05 g; 0.038 mol), was converted into its phosphine dichloride as in Example 7. The dichloride was dissolved in tetrahydrofuran and a solution of 7.66 g (0.0765 mol) of piperidine and 7.65 g (0.0765 mol) of triethylamine in tetrahydrofuran was added dropwise with stirring. After stirring for two hours, 1.22 g (0.0381 mol) of sulfur was added and the reaction stirred overnight. The reaction was then filtered and concentrated to dryness. The residue was dissolved in boiling methanol and centrifuged to remove the unreacted sulfur; the supernatant liquid was decanted and upon cooling, white crystals precipitated. The white crystals were filtered and dried to yield N-trifluoroacetyl-N-[bis(1-piperidino)phosphinothioylmethyl]glycine, ethyl ester (9.25 g), m.p. 150°-152° C., and having the following analysis:

Calculated: C, 43.12; H, 6.60; N, 14.79. Found: C, 43.18; H, 6.62; N, 14.79.

EXAMPLE 18

N-trifluoroacetyl-N-(hydroxyphosphinylmethyl)-glycine, ethyl ester, was converted into 11.2 g of its phosphine dichloride as in Example 7. The dichloride was dissolved in tetrahydrofuran and a solution of 6.40 g (0.0711 mol) of methoxycarbonylhydrazine and 7.18 g of triethylamine (0.0711 mol) in tetrahydrofuran was added dropwise with stirring. After stirring for two hours, 1.13 g (0.0353 mol) of sulfur was added and the reaction stirred overnight. The reaction was then filtered and concentrated to dryness. The residue was dissolved in methanol and centrifuged to remove the unreacted sulfur; the supernatant liquid was decanted and concentrated to dryness. The residue was dissolved in ether and washed with 5% aqueous sodium bicarbonate and hydrochloric acid, then dried over magnesium sulfate, filtered and concentrated to dryness. This residue was chromatographed on silica gel with ether to yield N-trifluoroacetyl-N-[bis(methoxycarbonylhydrazino)phosphinothioylmethyl]-glycine, ethyl ester, as a yellow solid, m.p. 56°-63° C., and having the following analysis:

Calculated: C, 29.14; H, 4.22. Found: C, 29.58; H, 4.21.

EXAMPLE 19

N-trifluoroacetyl-N-(hydroxyphosphinylmethyl)-glycine, ethyl ester (11.05 g), was converted into its phosphine dichloride as in Example 7. The dichloride was dissolved in tetrahydrofuran and a solution of 4.34 g of methylamine (0.14 mol) in tetrahydrofuran was added dropwise with stirring. After stirring for two hours, 1.12 g of sulfur was added and the reaction stirred overnight. The reaction was then filtered and concentrated to dryness. The residue was dissolved in methanol and centrifuged to remove the unreacted sulfur; the supernatant liquid was decanted and concentrated to dryness. The residue was chromatographed on silica gel with ether, then acetone to yield N-trifluoroacetyl-N-[bis(methylamino)phosphinothioylmethyl]glycine, ethyl ester (1.2 g), m.p. 68°-85° C. and having the following analysis:

Calculated: C, 32.24; H, 5.11; N, 12.53. Found: C, 32.62; H, 4.73; N, 11.88.

EXAMPLE 20

N-trifluoroacetyl-N-(hydroxyphosphinylmethyl)-glycine, ethyl ester (11.55 g), was converted into its phosphine dichloride as in Example 7. The dichloride was dissolved in tetrahydrofuran and a solution of 6.87 g (0.0735 mol) allylamine hydrochloride and 7.43 g (0.0735 mol) of triethylamine in tetrahydrofuran was added dropwise with stirring. After stirring for two hours, 1.17 g of sulfur was added and the reaction stirred overnight. The reaction was then filtered and concentrated to dryness. The residue was dissolved in methanol and centrifuged to remove the unreacted sulfur; the supernatant liquid was decanted and concentrated to dryness. The residue was dissolved in ether and washed with 5% aqueous sodium bicarbonate and hydrochloric acid, then dried over magnesium sulfate, filtered and concentrated to dryness. This residue was chromatographed on silica gel with dichloromethane to yield N-trifluoroacetyl-N-[bis(allylamino)phosphinothioylmethyl]glycine, ethyl ester (1.3 g), as a yellow oil, $N_D^{25}=1.4870$, and having the following analysis:

Calculated: C, 40.31; H, 5.46; N, 10.85. Found: C, 40.11; H, 5.55; N, 10.74.

EXAMPLE 21

N-trifluoroacetyl-N-(hydroxyphosphinylmethyl)-glycine, 2-chloro ethyl ester, was converted into 12 g of its phosphine dichloride as in Example 7. The dichloride was dissolved in tetrahydrofuran and a solution of 3.92 g (0.0688 mol) of allylamine and 6.95 g (0.0688 mol) of triethylamine in tetrahydrofuran was added dropwise with stirring. After stirring for two hours, 1100 mg of sulfur was added and the reaction stirred overnight. The reaction mixture was then filtered and concentrated to dryness. The residue was dissolved in methanol and centrifuged to remove the unreacted sulfur; the supernatant liquid was decanted and concentrated to dryness. The residue was dissolved in ether and washed with 5% aqueous sodium bicarbonate and hydrochloric acid, then dried over magnesium sulfate, filtered and concentrated to dryness to yield N-trifluoroacetyl-N-[bis(allylamino)phosphinothioylmethyl]glycine, 2-chloro ethyl ester hemihydrate (14.2 g) as an orange oil, $N_D^{25} = 1.5030$, and having the following analysis:

Calculated: C, 36.21; H, 4.87; N, 9.74. Found: C, 36.46; H, 4.91; N, 9.44.

EXAMPLE 22

N-trifluoroacetyl-N-(hydroxyphosphinylmethyl)-glycine, butyl ester, was converted into 10.3 g of its phosphine dichloride as in Example 7. The dichloride was dissolved in tetrahydrofuran and a solution of 4.618 g (0.063 mol) of sec-butylamine and 6.37 g (0.063 mol) of triethylamine in tetrahydrofuran was added dropwise with stirring. After stirring for two hours, 1.01 g of sulfur was added and the reaction stirred overnight. The reaction mixture was then filtered and concentrated to dryness. The residue was dissolved in methanol and centrifuged to remove the unreacted sulfur; the supernatant liquid was decanted and concentrated to dryness. This residue was dissolved in ether and washed with 5% aqueous sodium bicarbonate and hydrochloric acid, then dried over magnesium sulfate, filtered, concentrated to dryness and chromatographed on silica gel with 50% ligroin in dichloromethane (V:V) to yield N-trifluoroacetyl-N-[bis(sec-butylamino)phosphinothioylmethyl]-glycine, butyl ester, as a yellow oil, $N_D^{25} = 1.4665$, and having the following analysis:

Calculated: C, 45.63; H, 7.43; N, 9.39. Found: C, 45.80; H, 7.38; N, 9.43.

EXAMPLE 23

N-trifluoroacetyl-N-[bis(chloro)phosphinomethyl]glycine, ethyl ester (800 mg), was prepared as in Example 7. The phosphine dichloride was dissolved in 10 ml of tetrahydrofuran and to it a solution of 630 mg of N,N-dimethylhydrazine (0.0105 mol) containing 82 mg of sulfur in tetrahydrofuran was added. The reaction was stirred for one hour at room temperature and the hydrazine salts were removed by centrifugation. The supernatant was concentrated to an oil, dissolved in methanol and centrifuged to remove unreacted sulfur. The methanol soluble portion was decanted and concentrated to an oil, which was chromatographed on silica gel with ethyl acetate to yield N-trifluoroacetyl-N-[bis(N,N-dimethylhydrazino)phosphinothioylmethyl]glycine, ethyl ester (220 mg), as a yellow oil, $N_D^{25} = 1.4795$ and having the following analysis:

Calculated: N, 17.80; P, 7.87; S, 8.15. Found: N, 17.45; P, 7.58; S, 8.48.

EXAMPLE 24

When dimethylamine and sulfur are reacted with the phosphine dichloride of N-trifluoroacetyl-N-(hydroxyphosphinylmethyl)glycine, ethyl ester, in accordance with Example 7, one obtains N-trifluoromethylacetyl-N-[bis(dimethylamino)phosphinothioylmethyl]-glycine, ethyl ester, as an amber oil having the following analysis:

Calculated: N, 11.57; P, 8.52; S, 8.80. Found: N, 11.88; P, 8.81; S, 9.20.

EXAMPLE 25

When N-methylaniline is reacted with N-trifluoroacetyl-N-[bis(chloro)phosphinomethyl]glycine, ethyl ester, as in Example 9, one obtains N-trifluoroacetyl-N-[bis(N-methylanilino)phosphinothioylmethyl]-glycine, ethyl ester, as a yellow oil, $N_D^{25} = 1.5328$, and having the following analysis:

Calculated: C, 56.73; H, 6.52; N, 7.35. Found: C, 56.39; H, 6.47; N, 6.71.

EXAMPLE 26

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |

-continued

| | |
|---|---|
| J - Downy Brome | T - Crabgrass |

*Established from vegetative propagules.

TABLE I

| Compound of Example No. | WAT | kg/h | A | B | C | D | E | F | G | H | I | J | K |
|---|---|---|---|---|---|---|---|---|---|---|---|---|---|
| 1 | 5 | 11.2 | 2 | 1 | 0 | 2 | 1 | 1 | 0 | 1 | 3 | 0 | 2 |
| 1 | 5 | 5.6 | 1 | 1 | 1 | 2 | 2 | 1 | 0 | 1 | 2 | 0 | 2 |
| 2 | 4 | 11.2 | 2 | 2 | 1 | 2 | 3 | 2 | 1 | 1 | 2 | 1 | 3 |
| 3 | 4 | 11.2 | 2 | — | 0 | 2 | 1 | 1 | 2 | 2 | 2 | 2 | 3 |
| 3 | 4 | 5.6 | 1 | — | 0 | 2 | 1 | 1 | 2 | — | 1 | 3 | 3 |
| 4 | 4 | 11.2 | 0 | 0 | 0 | 1 | 0 | 0 | 0 | 0 | 0 | 0 | 0 |
| 4 | 2 | 5.6 | 0 | 0 | 0 | 0 | 0 | 0 | 0 | 0 | 0 | 0 | 0 |
| 5 | 4 | 11.2 | 0 | 0 | 0 | 2 | 2 | — | 0 | 1 | 0 | 0 | 2 |
| 5 | 2 | 5.6 | 0 | 0 | 0 | 1 | 1 | 0 | 0 | 0 | 0 | 0 | 2 |
| 6 | 2 | 11.2 | 0 | 0 | 0 | 0 | 0 | 0 | 0 | — | 0 | 0 | 0 |
| 6 | 2 | 5.6 | 0 | — | 0 | 0 | 0 | 0 | 0 | 0 | 0 | 0 | 0 |
| 7 | 4 | 11.2 | 1 | 1 | 1 | 1 | 1 | 2 | 1 | 2 | 2 | 1 | 2 |
| 7 | 4 | 5.6 | 1 | 2 | 1 | 1 | 1 | 1 | 2 | 2 | 2 | 2 | 2 |
| 8 | 4 | 11.2 | 4 | 3 | 2 | 2 | 2 | 4 | 3 | 2 | 2 | 2 | 2 |
| 8 | 4 | 5.6 | 2 | 2 | 0 | 1 | 1 | 1 | 2 | 2 | 1 | 1 | 2 |
| 9 | 4 | 11.2 | 1 | 1 | 1 | 1 | 1 | 2 | 1 | 1 | 1 | 1 | 2 |
| 9 | 2 | 5.6 | 0 | 0 | 0 | 0 | 0 | 0 | 0 | 0 | 0 | 0 | 1 |
| 10 | 4 | 11.2 | 1 | 1 | 1 | 1 | 2 | 2 | 2 | 3 | 3 | 2 | 2 |
| 10 | 4 | 5.6 | 1 | 2 | 1 | 1 | 2 | 1 | 2 | 2 | 3 | 2 | 2 |
| 11 | 4 | 11.2 | 0 | 1 | 0 | 1 | 0 | 0 | 0 | 0 | 1 | 0 | 1 |
| 11 | 2 | 5.6 | 0 | 0 | 0 | 0 | 0 | 0 | 0 | 0 | 0 | 0 | 1 |
| 12 | 4 | 11.2 | 1 | 1 | 1 | 1 | 4 | 2 | 2 | 1 | 2 | 2 | 3 |
| 12 | 4 | 5.6 | 1 | 0 | 1 | 1 | 3 | 2 | 1 | 1 | 1 | 2 | 3 |
| 13 | 4 | 11.2 | 2 | 2 | 2 | 2 | 4 | 2 | 1 | 1 | 0 | 3 | 3 |
| 13 | 4 | 5.6 | 1 | 2 | 2 | 2 | 2 | 2 | 0 | 1 | 1 | 2 | 3 |
| 14 | 4 | 11.2 | 2 | 2 | 1 | 2 | 4 | 4 | 1 | 2 | 1 | 2 | 3 |
| 14 | 4 | 5.6 | 2 | 2 | 2 | 2 | 4 | 2 | 1 | 1 | 1 | 2 | 3 |
| 15 | 4 | 11.2 | 0 | 0 | 0 | 1 | 1 | 0 | 0 | 0 | 1 | 0 | 1 |
| 15 | 2 | 5.6 | 0 | 0 | 0 | 0 | 0 | 0 | 0 | 0 | 0 | 0 | 0 |
| 16 | 4 | 11.2 | 1 | 1 | 0 | 2 | 3 | 0 | 1 | 0 | 0 | 0 | 2 |
| 16 | 2 | 5.6 | 0 | 1 | 0 | 1 | 1 | 0 | 1 | 0 | 0 | 0 | 1 |
| 17 | 4 | 11.2 | 0 | 2 | 0 | 2 | 1 | 0 | 0 | 0 | 0 | 0 | 1 |
| 17 | 2 | 5.6 | 0 | 0 | 0 | 0 | 0 | 0 | 1 | 0 | 0 | 0 | 1 |
| 18 | 4 | 11.2 | 0 | 2 | 1 | 2 | 0 | 1 | 1 | 0 | 0 | 0 | 3 |
| 18 | 2 | 5.6 | 0 | 1 | 0 | 1 | 0 | 1 | 0 | 0 | 0 | 0 | 1 |
| 19 | 4 | 11.2 | 3 | 3 | 1 | 2 | 1 | 1 | 1 | 1 | 3 | 1 | 3 |
| 19 | 4 | 5.6 | 1 | 3 | 1 | 1 | 1 | 0 | 1 | 0 | 1 | 0 | 1 |
| 20 | 4 | 11.2 | 1 | 1 | 0 | 1 | 0 | 0 | 1 | 0 | 0 | 0 | 1 |
| 20 | 2 | 5.6 | 0 | 0 | 0 | 1 | 0 | 0 | 1 | 0 | 0 | 0 | 1 |
| 21 | 4 | 11.2 | 4 | 2 | 1 | 1 | 2 | 0 | 2 | 1 | 2 | 1 | 3 |
| 21 | 4 | 5.6 | 2 | 1 | 1 | 1 | 2 | 0 | 2 | 4 | 3 | 1 | 3 |
| 22 | 2 | 11.2 | 0 | 0 | 0 | 0 | 0 | 0 | 0 | 0 | 0 | 0 | 1 |
| 22 | 2 | 5.6 | 0 | 0 | 0 | 0 | 0 | 0 | 0 | 0 | 0 | 0 | 0 |
| 23 | 4 | 11.2 | 4 | 3 | 4 | 3 | 4 | 4 | 1 | 1 | 1 | 2 | 4 |
| 23 | 4 | 5.6 | 3 | 3 | 3 | 2 | 4 | 3 | 2 | 3 | 1 | 1 | 4 |
| 24 | 4 | 11.2 | 2 | 3 | 2 | 2 | 4 | 2 | 1 | 2 | 1 | 3 | 3 |
| 24 | 4 | 5.6 | 3 | 3 | 1 | 2 | 3 | 1 | 1 | 3 | 1 | 1 | 3 |
| 25 | 2 | 11.2 | 0 | 0 | 0 | 0 | 1 | 0 | 0 | 0 | 0 | 0 | 1 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 2 | 4 | 5.6 | 1 | 0 | 2 | 0 | 1 | 1 | 1 | 1 | 0 | 0 | 0 | 0 | 0 | 1 | 1 | 1 |
| 2 | 2 | 1.12 | 1 | 0 | 0 | 0 | 0 | 0 | 0 | 0 | 0 | 0 | 0 | 0 | 0 | 0 | 0 | 0 |
| 2 | 2 | 0.28 | 0 | 0 | 0 | 0 | 0 | 0 | 0 | 0 | 0 | 1 | 0 | 0 | 0 | 0 | 0 | 1 |
| 3 | 4 | 5.6 | 1 | 1 | 1 | 0 | 1 | — | 0 | — | 1 | 2 | 1 | 0 | 1 | 3 | 2 | 3 |
| 3 | 2 | 1.12 | 0 | 0 | 0 | 0 | 0 | 0 | 0 | 1 | 1 | 1 | 0 | 0 | 0 | 0 | 0 | 1 |
| 7 | 4 | 5.6 | 1 | 1 | 3 | 2 | 2 | 2 | 1 | 1 | 2 | 2 | 2 | 1 | 1 | 3 | 3 | 3 |
| 7 | 4 | 1.12 | 1 | 2 | 0 | 0 | 1 | 1 | 0 | 1 | 0 | 1 | 1 | 0 | 0 | 1 | 1 | 2 |
| 7 | 2 | 0.28 | 1 | 0 | 0 | 0 | 0 | 1 | 0 | 1 | 0 | 0 | 0 | 0 | 0 | 0 | 0 | 0 |
| 8 | 4 | 5.6 | 1 | 3 | 3 | 3 | 3 | 3 | 1 | 1 | 2 | 3 | 3 | 3 | 3 | 4 | 4 | 4 |
| 8 | 4 | 1.12 | 1 | 2 | 1 | 1 | 2 | 1 | 0 | 1 | 1 | 3 | 2 | 1 | 1 | 2 | 3 | 3 |
| 8 | 2 | 0.28 | 1 | 0 | 0 | 0 | 0 | 1 | 0 | 1 | 0 | 1 | 0 | 0 | 0 | 1 | 1 | 2 |
| 12 | 4 | 5.6 | 1 | 2 | 3 | 2 | 2 | 2 | 1 | 2 | 4 | 4 | 3 | 2 | 1 | 4 | 3 | 3 |
| 12 | 4 | 1.12 | 1 | 0 | 0 | 1 | 0 | 0 | 0 | 2 | 1 | 2 | 1 | 0 | 0 | 1 | 3 | 3 |
| 13 | 4 | 5.6 | 2 | 2 | 4 | 3 | 3 | 2 | 1 | 2 | 2 | 4 | 1 | 2 | 3 | 4 | 4 | 3 |
| 13 | 4 | 1.12 | 1 | 0 | 1 | 0 | 2 | 1 | 0 | 1 | 0 | 0 | 0 | 0 | 2 | 2 | 2 | 2 |
| 13 | 2 | 0.28 | 0 | 0 | 1 | 0 | 0 | 0 | 0 | 1 | 0 | 2 | 0 | 0 | 0 | 0 | 0 | 0 |
| 14 | 4 | 5.6 | 1 | 2 | 3 | 2 | 3 | 2 | 1 | 3 | 2 | 4 | 3 | 3 | 3 | 4 | 4 | 4 |
| 14 | 4 | 1.12 | 0 | 1 | 1 | 0 | 1 | 0 | 0 | 2 | 1 | 2 | 0 | 0 | 2 | 2 | 2 | 3 |
| 14 | 2 | 0.28 | 0 | 0 | 1 | 0 | 0 | 0 | 0 | 1 | 0 | 2 | 0 | 0 | 1 | 0 | 1 | 2 |
| 18 | 4 | 5.6 | 1 | 1 | 2 | 2 | 2 | 2 | 2 | 2 | 1 | 4 | 1 | 2 | 4 | 4 | 3 | 3 |
| 18 | 2 | 1.12 | 1 | 0 | 2 | 0 | 0 | 1 | 1 | 1 | 1 | 0 | 1 | 1 | 0 | 0 | 1 | 2 |
| 19 | 4 | 5.6 | 2 | 1 | 2 | 2 | 3 | 2 | 2 | 3 | 1 | 1 | 1 | 2 | 3 | 3 | 3 | 3 |
| 19 | 2 | 1.12 | 0 | 0 | 1 | 0 | 0 | 1 | 0 | 1 | 0 | — | 0 | 0 | 0 | 0 | 1 | 3 |
| 19 | 2 | 0.28 | 0 | 0 | 0 | 0 | 0 | 0 | 0 | 1 | 0 | 0 | 0 | 0 | 0 | 0 | 0 | 1 |
| 21 | 4 | 5.6 | 1 | 1 | 2 | 1 | 2 | 2 | 2 | 2 | — | 3 | 3 | 2 | 2 | 3 | 3 | 4 |
| 21 | 3 | 1.12 | 0 | 0 | 2 | 1 | 2 | 0 | 0 | 1 | 1 | 1 | — | 0 | 2 | 3 | 3 | — |
| 21 | 3 | 0.28 | 0 | — | 0 | 0 | 1 | 4 | — | 1 | 4 | 3 | 2 | 0 | 2 | 1 | 1 | 1 |
| 24 | 4 | 5.6 | 2 | 2 | 2 | 1 | 3 | 2 | 1 | 1 | 1 | 3 | 1 | 1 | 1 | 1 | 2 | 3 |
| 24 | 4 | 1.12 | 1 | 1 | 1 | 0 | 1 | 1 | 1 | 1 | 0 | 1 | 0 | 1 | 0 | 1 | 1 | 1 |
| 24 | 2 | 0.28 | 1 | 0 | 0 | 0 | 1 | 0 | 0 | 0 | 0 | 0 | 0 | 0 | 0 | 0 | 1 | 1 |

EXAMPLE 27

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Tables III and IV.

The pre-emergent herbicidal activity index used below is based upon average percent control of each species as follows:

| Percent Control | Index |
|---|---|
| 0–24% control | 1 |
| 25–49% control | 1 |
| 50–74% control | 2 |
| 75–100% control | 3 |

Plant species in the tables are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| 1 | 5 | 11.2 | 0 | 0 | 0 | 0 | 3 | 0 | 0 | 0 | 0 | 1 | 1 |
| 2 | 2 | 11.2 | 1 | 0 | 0 | 0 | 2 | 0 | 0 | 3 | 0 | 0 | 0 |
| 3 | 2 | 11.2 | 0 | 0 | 0 | 0 | 0 | 0 | 0 | 0 | 0 | 0 | 2 |
| 5 | 2 | 11.2 | 3 | — | 0 | 0 | 1 | 0 | 0 | 1 | 0 | 0 | 2 |
| 6 | 2 | 11.2 | 0 | 0 | 0 | 1 | 0 | 0 | 0 | 0 | 3 | 0 | 0 |
| 8 | 2 | 11.2 | 1 | 0 | 0 | 0 | 0 | 0 | 0 | 1 | 0 | 0 | 0 |
| 10 | 4 | 11.2 | 1 | 0 | 0 | 0 | 0 | 0 | 1 | 1 | 0 | 0 | 0 |
| 12 | 2 | 11.2 | 1 | 0 | 0 | 0 | 1 | 0 | 1 | 2 | 1 | 1 | 1 |
| 13 | 4 | 11.2 | 3 | 0 | 1 | 1 | 3 | 0 | 0 | 2 | 0 | 0 | 2 |
| 14 | 4 | 11.2 | 2 | 0 | 1 | 1 | 3 | 0 | 0 | 3 | 0 | 2 | 3 |
| 16 | 2 | 11.2 | 1 | 0 | 0 | 0 | 1 | 0 | 0 | 0 | 0 | 0 | 0 |
| 17 | 2 | 11.2 | 1 | 0 | 0 | 0 | 0 | 0 | 1 | 1 | 0 | 0 | 0 |
| 19 | 4 | 11.2 | 3 | 0 | 0 | 1 | 3 | 0 | 1 | 2 | 0 | 1 | 0 |
| 20 | 2 | 11.2 | 1 | 0 | 0 | 0 | 3 | 0 | 0 | 1 | 0 | 0 | 1 |
| 21 | 2 | 11.2 | 1 | 0 | 0 | 0 | 0 | 0 | 0 | 1 | 0 | 0 | 1 |
| 22 | 2 | 11.2 | 1 | 0 | 0 | 0 | 0 | 0 | 0 | 1 | 0 | 0 | 0 |
| 24 | 2 | 11.2 | 3 | 0 | 1 | 2 | 1 | 0 | 0 | 3 | 0 | 3 | 2 |

TABLE IV

| Compound of | | | L | M | N | O | P | B | Q | D | R | E | F | C | J | S | K | T |
|---|---|---|---|---|---|---|---|---|---|---|---|---|---|---|---|---|---|---|
| 24 | 4 | 11.2 | 3 | 3 | 1 | 2 | 1 | 0 | 0 | 2 | 1 | 1 | 0 | 0 | 3 | 3 | 2 | 3 |
| 24 | 4 | 7.84 | 3 | 2 | 2 | 1 | 1 | 0 | 0 | 2 | 1 | 1 | 0 | 1 | 3 | 2 | 2 | 2 |
| 24 | 4 | 5.6 | 3 | 2 | 1 | 1 | 1 | 0 | 0 | 1 | 0 | 1 | 0 | 0 | 3 | 1 | 1 | 2 |
| 24 | 2 | 1.12 | 3 | 0 | 0 | 1 | 0 | 0 | 0 | 0 | 0 | 0 | 0 | 0 | 1 | 0 | 0 | 1 |
| 24 | 2 | 0.28 | 3 | 0 | 0 | 0 | 0 | 0 | 0 | 0 | 0 | 0 | 0 | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Tables III and IV, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

| | | |
|---|---|---|
| 1. N—trifluoroacetyl-N—[bis(dimethylamino)phosphinothioylmethyl]glycine, ethyl ester | 95 parts | |
| Methanol | 5 parts | |
| 2. N—trifluoroacetyl-N—[bis(isopropylamino)phosphinothioylmethyl]glycine, 2-chloroethyl ester | 95 parts | |
| Ethoxylated nonyl phenol | 5 parts | |
| 3. N—trifluoroacetyl-N—[bis(pyrrolidino)phosphinothioylmethyl]glycine, 2-ethoxyethyl ester | 90 parts | |
| Isopropanol | 10 parts | |
| 4. N—trifluoroacetyl-N—[bis(morpholino)phosphinothioylmethyl]glycine, octyl ester | 90 parts | |
| Ethoxylated octyl phenol | 10 parts | |
| 5. N—trifluoroacetyl-N—[bis(diallylamino)phosphinothioylmethyl]glycine, methyl ester | 90 parts | |
| Chloroform | 5 parts | |
| Ethoxylated dinonyl phenol | 5 parts | |
| 6. N—trifluoroacetyl-N—[bis(N—methyl-N—benzylamino)phosphinothioylmethyl]glycine, butyl ester | 75 parts | |
| Butanol | 25 parts | |
| 7. N—trifluoroacetyl-N—[bis(di-n-propylamino)phosphinothioylmethyl]glycine, ethyl ester | 75 parts | |
| Ethoxylated oleyl alcohol | 25 parts | |
| 8. N—trifluoroacetyl-N—[bis(n-propylamino)phosphinothioylmethyl]glycine, ethyl ester | 75 parts | |
| Acetonitrile | 15 parts | |
| Ethoxylated cocoamine | 10 parts | |
| 9. N—trifluoroacetyl-N—[bis(anilino)phosphinothioylmethyl)glycine, ethyl ester | 75 parts | |
| 1,2-Dimethoxyethane | 20 parts | |
| Ethoxylated tallow amine | 5 parts | |
| 10. N—trifluoroacetyl-N—[bis(butylamino)phosphinothioylmethyl]glycine, ethyl ester | 50 parts | |
| Dimethylformamide | 50 parts | |
| 11. N—trifluoroacetyl-N—[bis(diallylamino)phosphinothioylmethyl]glycine, ethyl ester | 50 parts | |
| Isopropyl dodecylbenzene sulfonate | 50 parts | |
| 12. N—trifluoroacetyl-N—[bis(pyrrolidino)phosphinothioylmethyl]glycine, ethyl ester | 50 parts | |
| Dimethylsulfoxide | 40 parts | |
| Ethoxylated soybeanamine | 10 parts | |
| 13. N—trifluoroacetyl-N—[bis(ethylamino)phosphinothioylmethyl]glycine, ethyl ester | 50 parts | |
| γ-butyrolactone | 25 parts | |
| Triethanolamine dodecylbenzene sulfonate | 25 parts | |
| 14. N—trifluoracetyl-N—[bis(isopropylamino)phosphinothioylmethyl]glycine, ethyl ester | 50 parts | |
| 1,1,1-Trichloroethane | 42 parts | |
| Ethoxylated nonyl phenol | 8 parts | |
| 15. N—trifluoroacetyl-N—[bis(cyclohexylamino)phosphinothioylmethyl]glycine, ethyl ester | 25 parts | |
| Chloroform | 75 parts | |
| 16. N—trifluoroacetyl-N—[bis(phenylhydrazino)phosphinothioylmethyl]glycine, ethyl ester | 25 parts | |
| Chloroform | 70 parts | |
| Ethoxylated tallow amine | 5 parts | |
| 17. N—trifluoroacetyl-N—[bis(1-piperidinyl)phosphinothioylmethyl]glycine, ethyl ester | 25 parts | |
| 1,1,1-Trichloroethane | 74 parts | |
| Ethoxylated oleyl alcohol | 1 part | |
| 18. N—trifluoroacetyl-N—[bis(methoxycarbonylhydrazino)phosphinothioylmethyl]glycine, ethyl ester | 25 parts | |
| Chloroform | 68 parts | |
| Ethoxylated dinonyl phenol | 7 parts | |
| 19. N—trifluoroacetyl-N—[bis(methylamino)phosphinothioylmethyl]glycine, ethyl ester | 10 parts | |
| Chloroform | 90 parts | |
| 20. N—trifluoroacetyl-N—[bis(allylamino)phosphinothioylmethyl]glycine, ethyl ester | 10 parts | |
| Methanol | 80 parts | |
| Polyoxypropylene - polyoxyethylene block copolymer | 10 parts | |
| 21. N—trifluoroacetyl-N—[bis(allylamino)phosphinothioylemthyl]glycine, 2-chloroethyl ester | 10 parts | |
| Ethanol | 88 parts | |
| Polyoxyethylene (20) sorbitan-monolaurate | 2 parts | |
| 22. N—trifluoroacetyl-N—[bis(sec-butylamino)phosphinothioylmethyl]glycine, butyl ester | 10 parts | |
| Isopropanol | 72 parts | |
| Polyoxyethylene sorbitan-monooleate | 18 parts | |
| 23. N—trifluoroacetyl-N—[bis(N,N—dimethylhydrazino)phosphinothioylmethyl]glycine, ethyl ester | 5 parts | |
| Dimethylformamide | 95 parts | |
| 24 N—trifluoroacetyl-N—[bis(N—methylanilino)phosphinothioylmethyl]glycine, ethyl ester | 5 parts | |
| Acetonitrile | 90 parts | |
| Ethoxylated tallow amine | 5 parts | |
| 25. N—trifluoroacetyl-N—[bis(dimethylamino)phosphinothioylmethyl]glycine, ethyl ester | 5 parts | |
| Ethanol | 94 parts | |
| Ethoxylated tallow amine | 1 part | |
| 26. N—trifluoroacetyl-N—[bis(n-propyl amino)phosphinothioylmethyl]glycine, ethyl ester | 5 parts | |
| Isopropanol | 80 parts | |
| Ethoxylated cocoamine | 15 parts | |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula $$RO-\underset{\underset{O}{\|}}{C}-CH_2\underset{\underset{\underset{CF_3}{|}}{\underset{\|}{O=C}}}{N}-CH_2-\underset{\underset{Z}{\diagdown}}{\overset{\overset{S}{\|}}{P}}\diagup Z$$

wherein R is a member of the group consisting of alkyl of from 1 to 8 carbon atoms, chloroalkyl of from 1 to 4 carbon atoms and from 1 to 3 chlorine atoms and alkoxyalkyl containing from 3 to 7 carbon atoms and wherein each Z is the same member of the class consisting of: a. —NHR' and $$-\underset{\underset{R'}{|}}{N}-R'$$

wherein each R' is individually selected from the class consisting of $C_1$-$C_4$ alkyl, $C_2$-$C_4$ alkenyl, $C_3$-$C_7$ cycloalkyl, benzyl or phenyl; b. a heterocyclic group selected from the class consisting of morpholine, pyrrolidine or piperidine; and c.

$$\underset{\underset{N-Z_1}{|}}{H}$$

group wherein $Z_1$ is a —NHR'' or $$N\underset{\diagdown R''}{\diagup R''}$$

group wherein R'' is $C_1$-$C_4$ alkyl or phenyl group; or a $$\underset{\underset{N-C-OCH_3}{|\ \|}}{H\ \ O}$$

group.

2. A compound of claim 1 wherein R is alkyl of from 1 to 4 carbon atoms.

3. A compound of claim 1 wherein R is ethyl.

4. A compound of claim 3 wherein Z is propylamino.

5. A compound of claim 3 wherein Z is isopropylamino.

6. A compound of claim 3 wherein Z is dimethylamino.

7. A herbicidal composition comprising a herbicidally effective amount of a compound of claim 1 and an inert diluent.

8. A herbicidal composition of claim 7 wherein R is alkyl of from 1 to 4 carbon atoms.

9. A herbicidal composition of claim 8 wherein R is ethyl.

10. A herbicidal composition of claim 9 wherein Z is propylamino.

11. A herbicidal composition of claim 9 wherein Z is isopropylamino.

12. A herbicidal composition of claim 9 wherein Z is dimethylamino.

13. A herbicidal method which comprises applying to the plant or the plant locus a herbicidally effective amount of a compound of claim 1.

14. A herbicidal method which comprises applying to the plant or the plant locus a herbicidally effective amount of a compound of claim 2.

15. A herbicidal method which comprises applying to the plant or the plant locus a herbicidally effective amount of a compound of claim 3.

16. A herbicidal method which comprises applying to the plant or the plant locus a herbicidally effective amount of a compound of claim 4.

17. A herbicidal method which comprises applying to the plant or the plant locus a herbicidally effective amount of a compound of claim 5.

18. A herbicidal method which comprises applying to the plant or the plant locus a herbicidally effective amount of a compound of claim 6.

19. A compound of the formula $$RO-\underset{\underset{O}{\|}}{C}-CH_2\underset{\underset{\underset{CF_3}{|}}{\underset{\|}{O=C}}}{N}-CH_2-\underset{\underset{Z}{\diagdown}}{\overset{\overset{S}{\|}}{P}}\diagup Z$$

wherein R is a member of the group consisting of alkyl of from 1 to 8 carbon atoms, chloroalkyl of from 1 to 4 carbon atoms and from 1 to 3 chlorine atoms and alkoxyalkyl containing from 3 to 7 carbon atoms and Z is N,N-dimethylhydrazino.

20. A herbicidal composition comprising a herbicidally effective amount of a compound of the formula $$RO-\underset{\underset{O}{\|}}{C}-CH_2\underset{\underset{\underset{CF_3}{|}}{\underset{\|}{O=C}}}{N}-CH_2-\underset{\underset{Z}{\diagdown}}{\overset{\overset{S}{\|}}{P}}\diagup Z$$

wherein R is a member of the group consisting of alkyl of from 1 to 8 carbon atoms, chloroalkyl of from 1 to 4 carbon atoms and from 1 to 3 chlorine atoms and alkoxyalkyl containing from 3 to 7 carbon atoms and Z is N,N-dimethylhydrazino.

21. A herbicidal method which comprises applying to the plant or to the plant locus a herbicidally effective amount of a compound of the formula $$RO-\underset{\underset{O}{\|}}{C}-CH_2\underset{\underset{\underset{CF_3}{|}}{\underset{\|}{O=C}}}{N}-CH_2-\underset{\underset{Z}{\diagdown}}{\overset{\overset{S}{\|}}{P}}\diagup Z$$

wherein R is a member of the group consisting of alkyl of from 1 to 8 carbon atoms, chloroalkyl of from 1 to 4 carbon atoms and from 1 to 3 chlorine atoms and alkoxyalkyl containing from 3 to 7 carbon atoms and Z is N,N-dimethylhydrazino.

* * * * *